(12) United States Patent
Errico et al.

(10) Patent No.: US 6,175,769 B1
(45) Date of Patent: Jan. 16, 2001

(54) SPINAL CORD ELECTRODE ASSEMBLY HAVING LATERALLY EXTENDING PORTIONS

(75) Inventors: Joseph P. Errico, Bedminster; Thomas J. Errico, Summit, both of NJ (US)

(73) Assignee: Electro Core Technologies, LLC, Summit, NJ (US)

( * ) Notice: Under 35 U.S.C. 154(b), the term of this patent shall be extended for 0 days.

(21) Appl. No.: 09/332,805

(22) Filed: Jun. 14, 1999

(51) Int. Cl.$^7$ .................................................. A61N 1/05
(52) U.S. Cl. ................................................. 607/117
(58) Field of Search ............................................. 607/117

(56) References Cited

U.S. PATENT DOCUMENTS 3,724,467 * 4/1973 Avery et al. ........................ 607/117
3,738,368 * 6/1973 Avery et al. ........................ 607/117
4,285,347 * 8/1981 Hess .................................... 607/117

* cited by examiner

Primary Examiner—William E. Kamm
(74) Attorney, Agent, or Firm—Joseph P. Errico, Esq.

(57) ABSTRACT

A spinal electrode for use in spinal cord stimulation having portions which are specifically provided for coupling the electrode to the adjacent spinal tissue so that displacement of the electrode cannot easily occur by normal bodily motion as is a failure mechanism of prior electrode designs. The distal end of the electrode which includes the electrical contacts also includes at least one laterally extending non-electrical portion. The extending portions are provided for receiving a suture or wire therethrough. The laterally extending portions may include a readily identifiable distinguishing feature, such as a color dye or a textural difference, so that it can be readily seen as a safe region through which a suture may be passed. Alternatively (or in addition), the laterally extending portions may include a through hole so that the tip of the electrode may be tied to the spinous process (or other spinal bone) by a wire.

9 Claims, 1 Drawing Sheet

SPINAL CORD ELECTRODE ASSEMBLY HAVING LATERALLY EXTENDING PORTIONS

BACKGROUND OF THE INVENTION

1. Field of the Invention

This invention relates generally to a device used in the treatment of neurological disorders, especially pain and motor dysfunction by electro-stimulation of the spinal cord, and more particularly to a novel electrode having integrally formed attachment means which permit more reliable positioning of the electrode relative to the spinal cord.

2. Description of the Prior Art

The use of electrical stimulation for the purposes of alleviating pain and the treatment of other neurological afflictions has been utilized for a number of years, and in many instances has become the standard of care. In new applications, as well, electrical stimulation of components of the nervous system continues to show significant therapeutic promise.

More particularly, in the spine, the original approach to electrical stimulation was to place multiple electrical leads directly onto the dura around the spinal cord. In such a procedure, the larninae of a sequence of vertebrae were removed so that the leads could be placed in a spaced apart relation along the central posterior axis of the spinal cord. This approach required a substantially invasive procedure in which bones and tissue were displaced or removed. In addition, the high frequencies of electrode migration from the target site or sites rendered the entire procedure suspect.

Subsequent iterations of spinal cord stimulation devices were implanted much less invasively, generally by percutaneous positioning. The first generations of this approach were immediately advantageous over the prior methods, insofar as they were carried out using local anesthetic as the electrodes were guided into position with the use of a fluoroscope. These early non-invasive procedures continued to use single lead electrodes, thus requiring a plurality of separate implantations. In addition, the leads would still easily become dislodged and migrate from the desired treatment site, usually becoming ineffective, but sometimes having actively negative effects on other nerves. These limitations and failures associated with multiple implantations of single lead electrodes briefly caused a reversion to the older, more invasive approach.

In an attempt to unify the multiple leads necessary for spinal cord stimulation into a single electrode, thereby attempting to bring the state of the art back to non-invasive procedures, designs from the cardiovascular art, i.e. pacemakers, et al., were modified for use in the spine. Multiple lead electrodes had been used in the cardiovascular field for some time, and were generally designed to provide stimulation to a variety of points on the surface of the heart. The modifications of these leads included strengthening the both the leads and the structure containing the leads for the stresses of the spine, reducing the diameter of the leads to a size more appropriate for use in the spine, and alternatively providing either a removeable or permanent rigid wire within the electrode to enhance placement. Unfortunately, while eliminating some of the causes associated with electrode migration, and reducing the number of electrodes which could migrate, the advances did not address the fundamental inability to fix the electrode at the appropriate location.

Subsequent limited attempts to identify ways to stabilize the electrode at a specific location in the spine have been limited to integrating a fabric material into the terminal pad portion of the electrode, which fabric extends laterally out from the elastomeric pad portion, through which the surgeon may suture the electrode to the surrounding tissue. Unfortunately, surgeons generally prefer to suture through the more substantial elastomeric material of the terminal pad, thereby risking damaging the electrical contacts and leads therein.

Accordingly, it is an object of the present invention to provide a spinal cord stimulator assembly which reduces the incidence and complications associated with the migration of the electrode.

Correspondingly, it is also an object of the present invention to provide a spinal cord stimulator assembly which permits attachment of the electrode to surrounding soft tissue while minimizing the risk of inadvertent damage to the electrical contacts and thin wire leads of the device.

SUMMARY OF THE INVENTION

The preceding expressed object is provided in the present invention, which comprises new and novel embodiments of electrode and vertebral attachment devices for use in spinal cord stimulation, and which may be used in conjunction with standard and/or advanced electrical signal sources. More particularly, a variety of different embodiments of the present invention are contemplated, preferred ones of which are disclosed herein, including electrode assemblies having terminal pads which comprise laterally extending elastomeric material which does not include any electrically active materials, and which is ideal for receiving a suture, therethrough. These laterally extending suture receiving portions may further be color coded by the inclusion of a readily discernable dye by which the surgeon may easily recognize the safe portions of the terminal pad through which he may suture. These laterally extending suture pads may further (or alternatively) include small through holes which the surgeon may insert guidewires or other fastening devices for anchoring the electrode to surrounding bony tissue through which the surgeon would not otherwise be able to suture.

The electrode designs of the present invention have some similar features to those of the prior art, and more particularly, they each comprises a plurality of thin wire leads which are encased within a flexible elastomeric sheath. The wire leads may be wound in a tight helix in the elastomeric sheath so that the structure remains flexible in the axial as well as transverse directions. In addition, the wound structure may permit the inclusion of a selectively removeable rigid wire backbone by which the surgeon may manipulate the electrode into proper position. Each of said wire leads is coupled to a corresponding individual electrical contact located at the proximal end of the sheath. These contacts are coupled to the electrical signal generator which provides the potential to the distal tip which is placed adjacent to the spinal cord (or other target nerve group).

More particularly, the distal end of the electrode comprises a series of electrical terminals, generally equivalent in number to the number of electrical contacts at the proximal end (one terminal at the distal end and one electrical contact in the proximal end are preferably individually coupled to one another by one wire lead, each coupled set being in electrical isolation with the other sets so that each may carry a different potential). The terminals and the portion of the elastomeric sheath which contains them may be cylindrical (as is the rest of the sheath), however, it is preferred in the present invention that it be flattened out, forming a planar pad structure. The planar terminal pad generally includes a series of individual terminals which are generally circular and planar. As suggested above, the terminal pads are spaced apart from one another so that they are in at least partial electrical isolation from one another. The application of a voltage differential across the pads (by the coupling of the corresponding electrical contacts to different, or variable, voltage sources) causes a current to flow through the adjacent tissue. This current causes the disruption of pain signals in the target nerve roots, thus alleviating pain.

The terminal pad portion of the present invention, and specifically the new and novel features thereof, include means for attaching the pad to surrounding tissue. More particularly, in a first embodiment, the terminal pad includes at least one laterally extending portion which is formed of the same elastomeric material as the sheath in which the wire leads are encased. This at least one laterally extending portion preferably includes multiple symmetric laterally extending portions. These portions are provided so that the surgeon may suture the terminal pad to soft tissue matter which is adjacent to the desired target nerve site. In a first preferred variation of this embodiment, the laterally extending portions of the terminal pad, which is the portion through which the sutures are to be placed, includes a color coding which is visually distinct from the portion of the terminal pad which includes the electrical terminals (generally this portion is transparent—or at least a colorless translucent material). This distinct coloring provides the surgeon with a readily apparent target through which he or she can have a high level of confidence that the suture will not disrupt electrical signalling, or introduce a loss of integrity to the fluid barrier between the electrical components and the patient's fluids.

In a second embodiment, which may also include the color scheme described above, the laterally extending suture portions each include at least one through hole formed therein. The through holes are provided so that the surgeon may advance a wire (or other suitable attaching means) through the holes and then around (or through) an adjacent structure which is not suitable for suturing, such as a bone. In the spinal applications which are prevalent, the though holes may be suitable for wiring the electrode to the spinous process, the transverse process, or the lamina itself.

By techniques already known in the field of spinal surgery, the surgeon would place the electrode beneath the lamina in much the same way as is presently practiced with prior art electrodes. By this it is meant that the electrode may be inserted between two lamina and advanced forward and upwardly along the channel of the spinal cord. There are preferably a multiplicity of laterally extending portions of the terminal pad section of the electrode such that the terminals may be positioned at the desired locations within the spinal canal while still exposing at least one of the laterally extending suture pads within the adjacent lamina spaces. At this time the surgeon identifies a suitable tissue structure to which the electrode may be sown, for example a ligament in the facet joint, or muscle tissue overlying the posterior of the spinal column. The surgeon then sutures the electrode to that tissue. Alternatively, if the most suitable structure to which the electrode can b coupled is a bone, for example the spinous process, then the electrode should be coupled to the bone by means of the through hole and wire. This action secures the electrode against backing out of the spinal canal, thus preventing a principal failure mechanism of the spinal cord stimulator electrodes of the prior art.

A BRIEF DESCRIPTION OF THE DRAWINGS

THE DETAILED DESCRIPTION OF THE PREFERRED EMBODIMENTS

While the present invention will be described more fully hereinafter with reference to the accompanying drawings, in which particular embodiments are shown, and with respect to methods of implantation, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
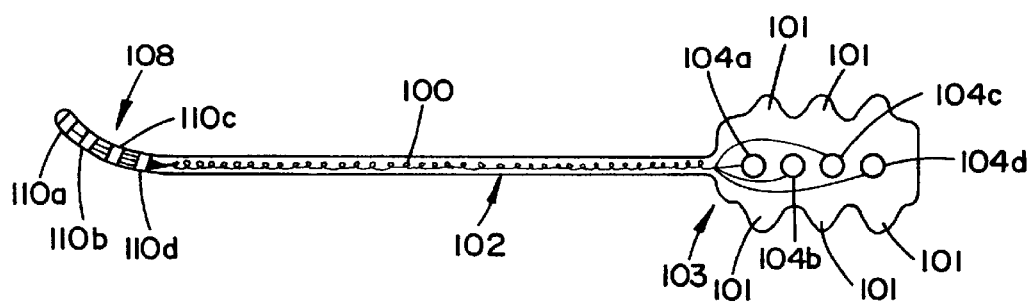
FIG. 1 shows a perspective view of an electrode having an terminal pad portion including laterally extending portions which are an aspect of the present invention.

Referring now to FIG. 1, the present invention comprises a spinal cord stimulation electrode having laterally extending portions 101 of the terminal pad section 103. The laterally extending portions 101 are provided so that the surgeon may have a structural portion through which he or she may safely introduce a suture to anchor the electrode so that it is prevented from migrating from the desired site. Although not easily illustrated in the present illustration, it is preferred that the laterally extending portions 101 be visually identifiable as being distinct from the rest of the terminal pad portion 103. This is desirable because the remainder of the terminal pad contains the electrical contacts and wires which should remain undisrupted or at least unexposed.

More particularly, this embodiment of the present invention comprises a plurality of thin wires 100 which are wound in tight helices, but which are insulated from one another such that they each may carry a different electrical potential. The wires 100 are encased in an elastomeric sheath 102 so that the structure remains flexible in the axial as well as transverse directions and so that destructive deformation of the wires 100 is minimized in conjunction with movement. (Although not shown, the wound structure may permit the inclusion of a rigid wire, which may be slideably inserted or removed from the electrode by the surgeon, and which provides the rigidity necessary during initial implantation and advancement into the spinal canal.) At the proximal end 108 of the electrode, the wire leads 100 are disposed in such a way that they may be individually coupled to voltage sources. In the present illustration, the electrical contacts 110a–d are designed as circumferential bands, however, it shall be understood that this conformation is not the only suitable one. More particularly, the only requirement for the proximal contacts is that stated hereinabove, i.e. that each wire be coupleable to a different voltage source. This permits a current to flow through the tissue against which the distal terminal pad section 103 is placed.

Referring again to the terminal pad 103 of the distal portion of the electrode, each of said wire leads 100 is coupled to a corresponding individual contact terminal (shown here as four linearly spaced planar pads 104a–d) located at the distal end 106 of the sheath 102. This terminal portion 103 is planar and forms a thin ribbon-like-structure. The entire portion 103 is encased in an insulating elastomeric material, for example a silicone or polyethylene. While this material may be of any color or texture, it is preferred that the material be transparent such that the integrity of the wires and the contact terminals may be visually inspected therethrough.

In this invention, the contact terminal 103 further includes a plurality of laterally extending portions 101 which are substantially separated from the portion of the terminal pad which contains the wire leads 100 and the contact terminals 104*a–d*. These laterally extending portions 101 are provided with a texture and/or color coding (generically shown in FIG. 1 as shaded regions) so that the surgeon may easily visually identify them. They are also sufficiently thick and durable enough so that the passage of a needle and suture material therethrough will not destroy the integrity of the material. More importantly, the material must be sufficiently tear resistant so that coupling of the laterally extending portion 101 to a adjacent tissue structure will not cause the suture to wear or tear through the portion.

Figure 2:
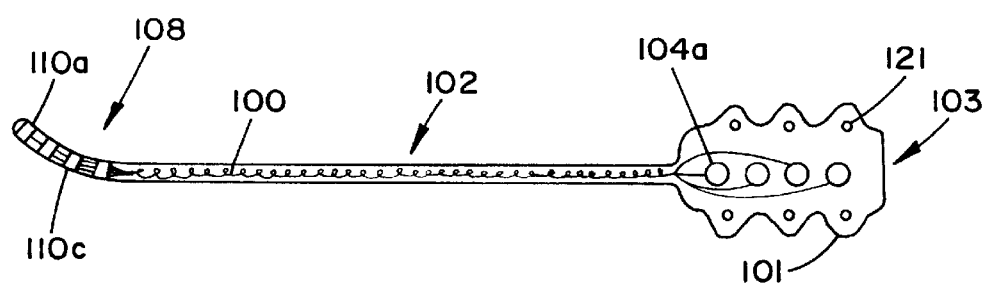
FIG. 2 shows a side perspective view of another electrode of the present invention wherein the laterally extending portions include through holes.

Suturing of the electrode to the adjacent soft tissue is not the only possible, and is often not even the desired, means of securing the electrode in place. In these cases it is often a solution to secure the electrode to a bone structure which is adjacent to the electrode target site. Referring now to FIG. 2, in which a variation of the present invention is provided, an alternative attachment facilitating design includes means for reliably receiving the bone securing mechanism. All relevant components of this embodiment are the same as the first embodiment described above. It is only the laterally extending portions which are different. More particularly, the bone securing device of choice in this area of the art is a metal wire order to receive this wire, the electrode variation of the present invention presently shown in FIG. 2 includes a through hole provided in each of the laterally extending portions 121.

Figure 3:
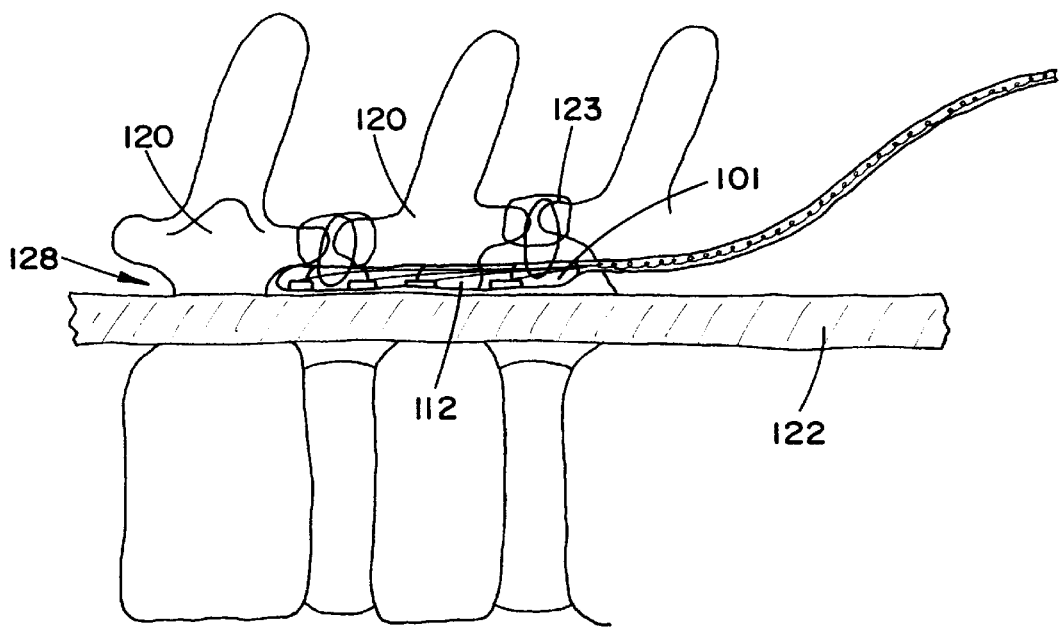
FIG. 3 shows a top perspective view of the electrode, first shown in FIG. 1, coupled to a ligament of the adjacent facet joint of an exemplary cutaway illustration of a human spine in a manner intended for the present invention.

More particularly, with respect to FIG. 3, the presently discussed embodiments of the invention are intended, in one application, to be inserted between the laminae 120 of two adjacent vertebrae and advanced along the spinal canal until its distal tip 112 can be withdrawn at the next space between sequential laminae. In this position, the terminal pads 104*a–d* are disposed against the dura of the spinal cord 122, underneath the lamina. This is the desired position for the electrode to apply the most direct electric field to the target nerves. The laterally extending portions 101 (or in conjunction with the embodiment of FIG. 2 laterally extending portions 121) which are exposed and are readily accessible between the lamina are then identified. A suture (or, in conjunction with the alternative embodiment shown in FIG. 2, a wire) is then coupled through the portion 101 and through an adjacent tissue, shown here as the posterior spinal musculature 123. (In conjunction with the embodiment of FIG. 2, a wire can be tied around the spinous process, the lamina itself, or a component of the facet joint. Alternatively, the wire can be coupled to a bone immobilizing implant such as a pedicle screw, hook, rod, cross connector device, et al.). This action secures the electrode against backing out and down the spinal canal 128.

While there has been described and illustrated specific embodiments of new and novel electrical stimulation implant devices, it will be apparent to those skilled in the art that variations and modifications are possible without deviating from the broad spirit and principle of the present invention which shall be limited solely by the scope of the claims appended hereto.

We claim:

1. A spinal stimulation electrode comprising:

a flexible and electrically insulating sheath, said sheath having a proximal end and a distal end;

a plurality of wire leads extending within said sheath, from said proximal end to said distal end;

a plurality of electrical contacts formed at the proximal and distal ends of said sheath, the contacts at the proximal end being coupled to the contacts at said distal end by said wire leads; said distal end of said sheath further including an electrical contact containing portion and at least one laterally extending portion, for receiving therethrough a means for coupling said distal portion to an adjacent tissue.

2. The spinal stimulation electrode as set forth in claim 1, wherein said at least one laterally extending portion further includes a through hole.

3. The spinal stimulation electrode as set forth in claim 1, wherein said at least one laterally extending portion comprises means for being readily distinguished from the electrical contact containing portion.

4. The spinal stimulation electrode as set forth in claim 3, wherein said means for being readily distinguished is selected from the group of sensory distinguishing features consisting of color dyes, textures, and topology.

5. The spinal stimulation electrode as set forth in claim 1, wherein said at least one laterally extending portion comprises a through hole for receiving therethrough a wire for securing said distal portion to a bone.

6. A spinal stimulation electrode for implantation within a human body, adjacent to nerve tissue, comprising:

a plurality of wire leads having electrical contacts formed at the ends thereof for placement adjacent to the nerve tissue;

a sheath for containing said wire leads, said sheath having a distal end which includes the electrical contacts;

said distal end of said sheath further including at least one laterally extending portion for coupling the electrode to non-nervous tissue which is adjacent to said nerve tissue.

7. The spinal stimulation electrode as set forth in claim 6, wherein the at least one laterally extending portion comprises a through hole.

8. The spinal stimulation electrode as set forth in claim 6, wherein the at least one laterally extending portion comprises means for being readily distinguished from the remainder of the distal portion.

9. The spinal stimulation electrode as set forth in claim 8, wherein said means for being readily distinguished is selected from the group of sensory distinguishing features consisting of color dyes, textures, and topology.

\* \* \* \* \*